(12) United States Patent
Lazar

(10) Patent No.: US 10,631,892 B2
(45) Date of Patent: Apr. 28, 2020

(54) INTERCHANGEABLE HAND TOOL

(71) Applicant: John Lazar, Bellport, NY (US)

(72) Inventor: John Lazar, Bellport, NY (US)

(*) Notice: Subject to any disclaimer, the term of this patent is extended or adjusted under 35 U.S.C. 154(b) by 6 days.

(21) Appl. No.: 15/456,148

(22) Filed: Mar. 10, 2017

(65) Prior Publication Data

US 2018/0256186 A1    Sep. 13, 2018

(51) Int. Cl.
| | | |
|---|---|---|
| *A61B 17/3201* | (2006.01) | |
| *B25F 1/02* | (2006.01) | |
| *B25F 1/00* | (2006.01) | |
| *A61B 17/54* | (2006.01) | |
| *A45D 29/02* | (2006.01) | |
| *A61B 17/00* | (2006.01) | |

(52) U.S. Cl.
CPC .......... *A61B 17/3201* (2013.01); *A45D 29/02* (2013.01); *B25F 1/003* (2013.01); *B25F 1/02* (2013.01); *A61B 17/54* (2013.01); *A61B 2017/00464* (2013.01)

(58) Field of Classification Search
CPC .. A61B 2017/0046; A61B 2017/00464; A61B 2017/00469; A61B 2017/00473; A61B 2017/2931; A61B 2017/294; A61B 17/3201; A61B 17/54; A61B 17/28; A61B 17/2804; A61B 17/2812; A61B 17/2816; A61B 17/282; A61B 17/285; A61B 17/29; A61B 2017/2825; B25F 1/02; B25F 1/003; B25F 1/006; B25F 1/00–04; A45D 29/18; A45D 29/02–2029/026; B25B 7/02–04; B25B 7/18; B25B 7/00–22; A61L 317/28; A61L 317/2804; A61L 317/2812; A61L 317/282; A61L 317/285; A61L 317/29; A61L 2017/2825

USPC ........... 81/300, 385, 386, 387, 388
See application file for complete search history.

(56) References Cited

U.S. PATENT DOCUMENTS

| | | | | |
|---|---|---|---|---|
| 3,681,840 A * | 8/1972 | Pool | ...................... | B25B 27/205 29/229 |
| 4,708,034 A * | 11/1987 | Oetiker | ..................... | B25B 7/00 81/9.3 |
| 5,664,274 A * | 9/1997 | Collins | ................... | B25F 1/003 224/904 |
| 6,012,362 A * | 1/2000 | Wang | ....................... | B25B 7/02 81/368 |
| 6,023,805 A * | 2/2000 | Lin | ......................... | B25F 1/003 7/118 |
| 6,108,845 A * | 8/2000 | Hung | ....................... | B25F 1/02 30/260 |
| 2001/0007172 A1 * | 7/2001 | Rinaldi | ................. | A45D 29/02 30/28 |
| 2009/0078278 A1 * | 3/2009 | Tran | ...................... | A45D 29/02 132/75.5 |
| 2014/0041195 A1 * | 2/2014 | Hoang | .................... | B25B 7/12 29/434 |

* cited by examiner

*Primary Examiner* — Katrina M Stransky
*Assistant Examiner* — Brigid K Byrd
(74) *Attorney, Agent, or Firm* — Michael J. Feigin, Esq.; Feigin and Fridman LLC

(57) ABSTRACT

This invention is an interchangeable hand tool device for surgical and other applications. The device includes an adjustable, interchangeable first jaw; an adjustable, interchangeable second jaw; a base to which the first and second jaws are attached; a central pivot about which one or both jaws can rotate; an interchangeable first handle connected to the base; an interchangeable second handle connected to the base.

16 Claims, 5 Drawing Sheets

Figure 5
Figure 6
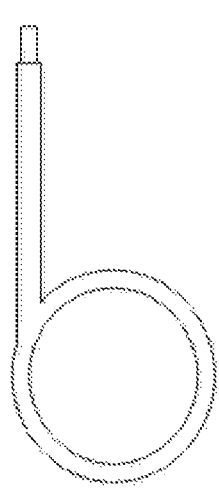
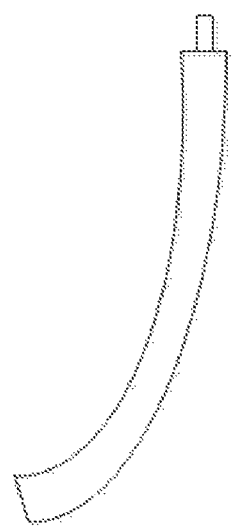
Figure 7
Figure 8

INTERCHANGEABLE HAND TOOL

BACKGROUND

During surgery, doctors may require access to many different tools and instruments, such as scalpels, lancets, scissors, injection needles, forceps, clamps, retractors, probes, and suction tubes. Space to store the wide assortment of tools that may be needed on short notice can pose a significant problem. Doctors and surgical teams may be forced to choose a limited array of tools to be within easy reach during surgery, and this selection may not be adequate for all situations that can occur.

Various devices exist for reducing the need to switch tools during surgery or making switching tools easier, particularly in minimally-invasive surgical procedures where the tools may be manipulated while within a patient's body. U.S. Pat. No. 8,088,026 describes methods and devices for interchangeable endoscopic end effectors. US patent publication number 2009/0209947 A1 describes systems and methods for interchangeable tips and tool box for assisting surgical procedures. Such devices and publications have the drawbacks that they are limited to electrically-powered devices and are especially designed for surgical tools only. It would be useful to have interchangeable tools that are mechanically operated and have a wider field of application than a particular class of surgical procedures.

Some devices currently exist for interchangeable hand tools. U.S. Pat. No. 5,471,698 describes a hand tool having interchangeable accessories. This patent has the drawbacks that it is only directed towards tools that are large enough to require a forearm brace, and it is directed toward a narrow scope of applications such as scraping a surface. U.S. Pat. No. 5,915,482 describes a hand tool with interchangeable attachments. This patent has the drawbacks that it is directed specifically to garden tools and it utilizes a large dowel-style handle. U.S. Pat. No. 6,983,506 describes a universal, interchangeable tool attachment system. This patent has the drawbacks that it does not include tools for surgical applications, and the interchangeability utilizes a pin system which may be slow and cumbersome to change tools and has small parts that might become easily lost.

It would be useful to have a hand tool device with interchangeable parts that is small enough to be hand-held, has a diverse field of applications including surgical procedures, has an interchangeability system that allows for fast part replacement and interchange, and does not rely on small parts for interconnection.

SUMMARY

In one aspect of the present invention, an interchangeable hand tool device for surgical and other applications is described. The device may include: an adjustable, interchangeable first jaw; an adjustable, interchangeable second jaw; a base to which the first and second jaws are attached; a central pivot about which one or both jaws can rotate; an interchangeable first handle connected to the base; an interchangeable second handle connected to the base; and an optional spring.

These and other features, aspects, and advantages of the present invention will become better understood with reference to the following drawings, description, and claims.

BRIEF DESCRIPTION OF THE DRAWINGS

FIG. 5 is a top view of a pliers jaw component of an embodiment of the device.

FIG. 6 is a top view of a scissors blade jaw component of an embodiment of the device.

FIG. 7 is a top view of a scissors handle component of an embodiment of the device.

FIG. 8 is a top view of a pliers handle component of an embodiment of the device.

DETAILED DESCRIPTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention generally comprises a first and second jaw connected to a base, a central pivot within the base that allows for rotation of one or both jaws, a first and second handle connected to the base, and an optional spring connected to the first and second handle to provide tension.

Figure 1:
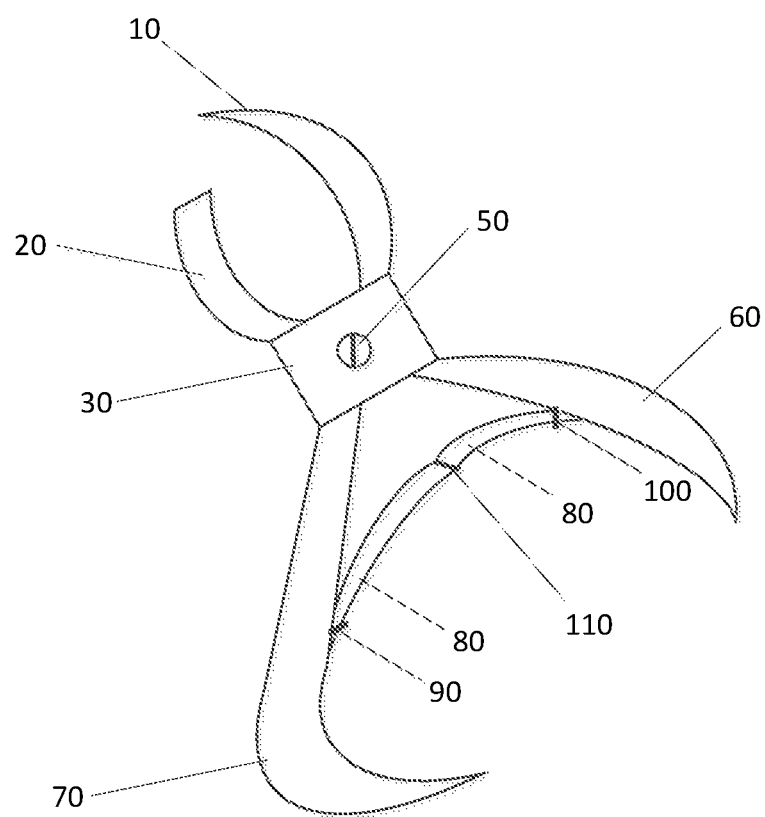
FIG. 1 is a top view of an embodiment of the device.

FIG. 1 is a top-view schematic diagram illustrating an example embodiment of the device. As shown, the example embodiment comprises a blade 10, a base 30, a jaw 20, a central pivot 50, a top handle 60, a bottom handle 70, and a spring 80.

Figure 2:
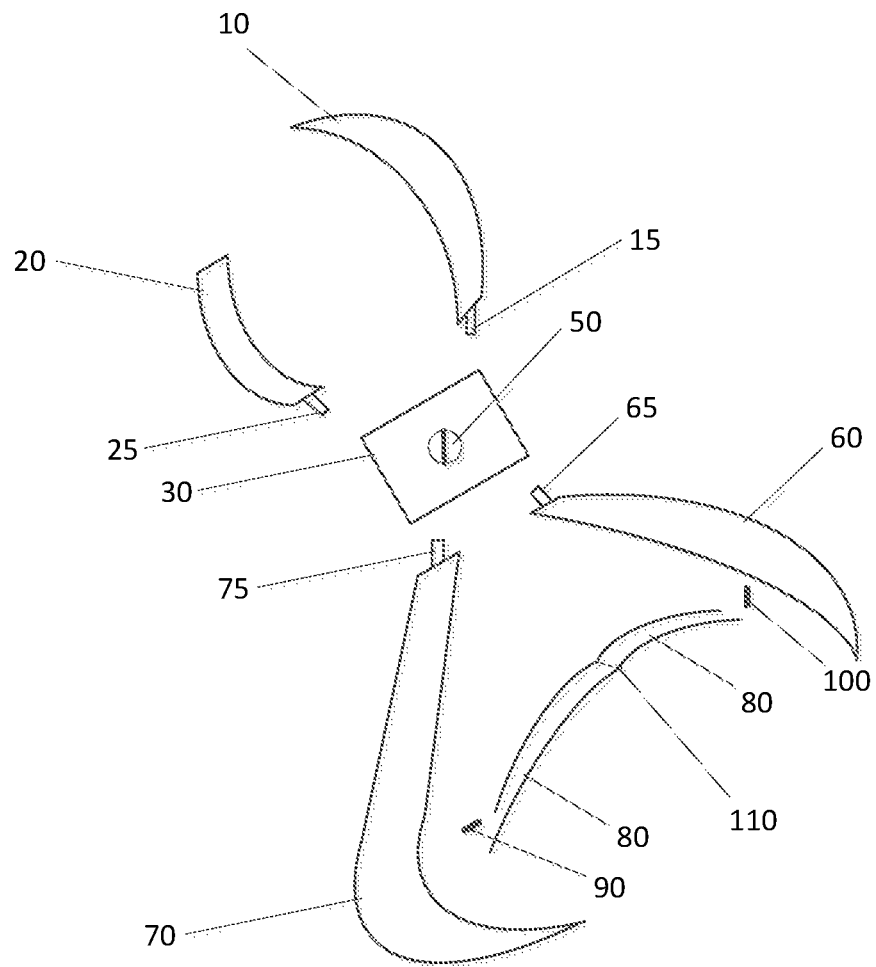
FIG. 2 is an exploded top view of an embodiment of the device.
Figure 3:
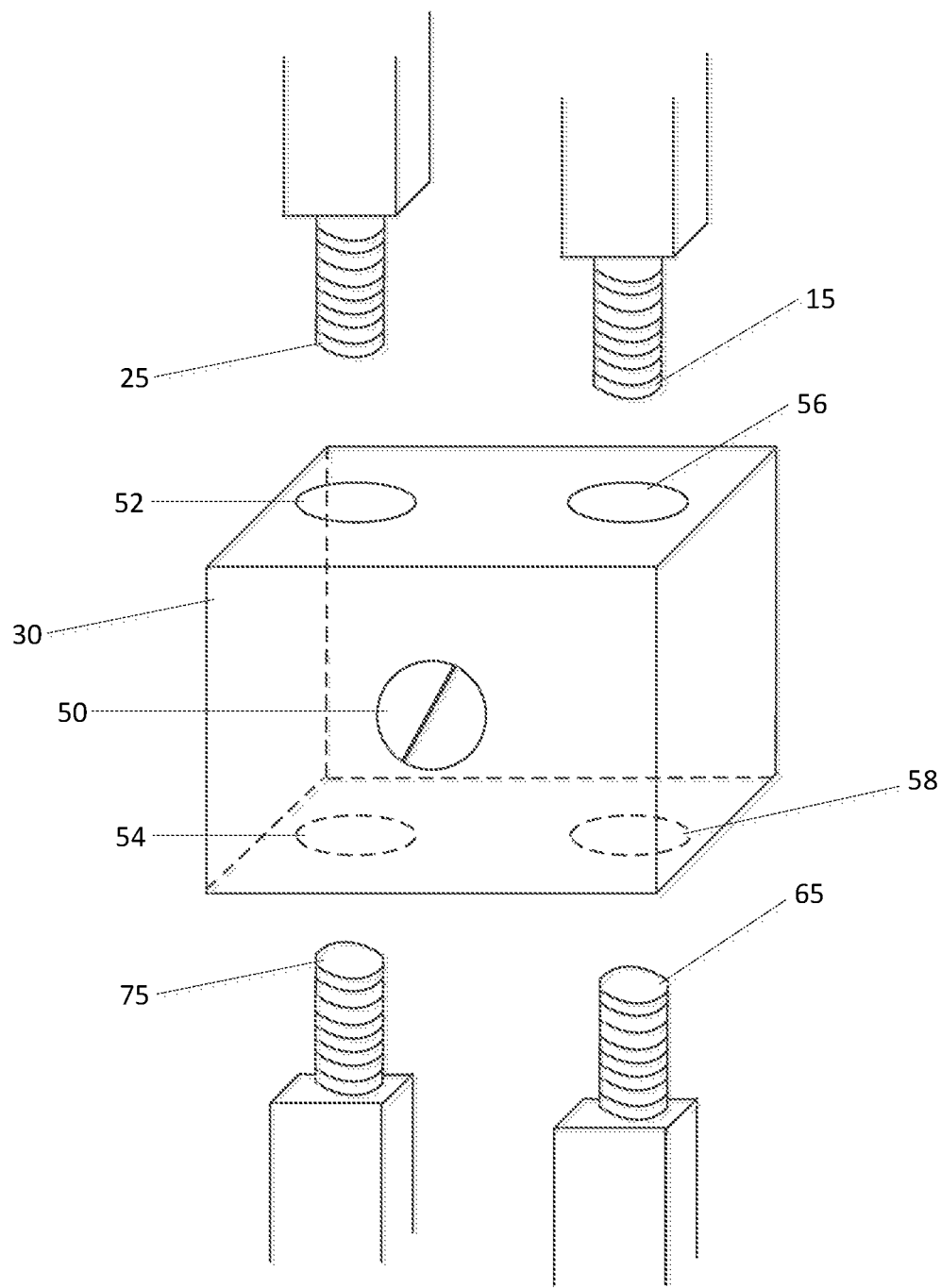
FIG. 3 is a close-up isometric view of the base and connections portion of an embodiment of the device.

Blade 10 is a standard angle blade that is sharp only along a single edge. Blade 10 is sharpened enough to debulk nails, without being excessively sharp so as to pose a danger to piercing skin. Blade 10 is attached to and removable from base 30, as illustrated in FIG. 2, by means of connector 15. Connector 15, as shown in FIG. 3, is a threaded screw-type connector that is inserted and rotated into connection receiver 56. Blade 10 is adjustable in angle of connection by tightening or loosening of connector 15. It should be understood that alternate configurations of blade 10 are contemplated, such as a scissors blade or pliers jaw.

Jaw 20 is a generally rectangular-shaped component that is curved toward blade 10. Jaw 20 is composed of a hard but slightly malleable material such as plastic or rubber. Jaw 20 is attached to and removable from base 30 by means of connector 25 and show in FIG. 2. Jaw 20 is adjustable in angle of connection by tightening or loosening of connector 25. It should be understood that alternate configurations of jaw 20 are contemplated, such as a scissors blade or pliers jaw.

The surface of jaw 20 that faces blade 10 is a curved surface composed of rubber, plastic, or another suitable material such as malleable steel that allows skin to rest against the surface without significant movement or slipping. Jaw 20 is sized and shaped appropriately to allow for a toe to be propped against it for debulking by blade 10.

Figure 4:
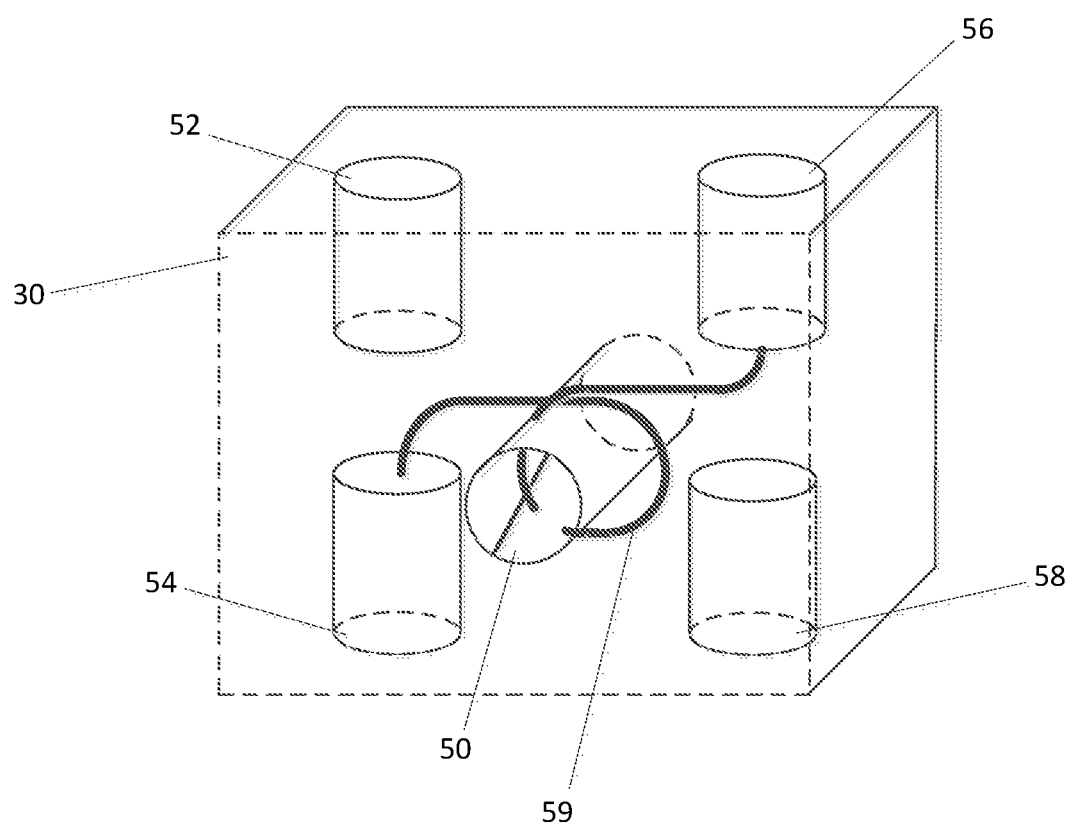
FIG. 4 is a close-up isometric view of the internals of the base portion of an embodiment of the device.

Base 30 is a generally rectangular-shaped component that is composed of a hard material such as plastic or metal. As shown in FIG. 3, base 30 has connection receivers 52, 54, 56, and 58. As shown in FIG. 4, these connection receivers are cylindrical holes with threading to receive and secure threaded screw-type connectors.

As shown in FIG. 4, central pivot 50 is a pivotal machine screw inserted horizontally through the center of base 30. Base 4 also contains looped wire 59, which is a piece of rigid wire that is permanently fixed to connection receiver 54 and connection receiver 56. Looped wire 59 is looped about central pivot 50 such that actuation of connection receiver 54 (and its connected component) causes rotation of connection receiver 56 (and its connected component) about central pivot 50. This allows blade 10 and bottom handle 70 to rotate about central pivot 50. It should be understood that alternate configurations of the internal components of base 4 are contemplated, including different means of connecting connection receivers 54 and 56 (such as a single rigid component that is welded, soldered, glued, or otherwise attached to the connection receivers), and different means of allowing rotation about central pivot 50 (such as a rigid component with a hole through which central pivot 50 is inserted).

Top handle 60 is a curved component that is shaped to be comfortable when held in a hand. Top handle 60 is composed of a firm, resilient material such as plastic, metal, or rubber. Top handle 60 is connected to base 30 by means of connector 65, as shown in FIG. 2. Top handle 60 is optionally connected to spring 80 by means of spring connector 100. It should be understood that alternate configurations of top handle 60 are contemplated, including different shapes for alternate tool configurations (such as grippable handles for pliers or finger-insertable handles for scissors), and different material composition or coverings (such as rubber for grip enhancement).

Bottom handle 70 is a curved component that is shaped to be comfortable when held in a hand. Bottom handle 70 is composed of a firm, resilient material such as plastic, metal, or rubber. Bottom handle 70 is connected to base 30 by means of connector 75 as shown in FIG. 2. Bottom handle 70 is optionally connected to spring 80 by means of spring connector 90. It should be understood that alternate configurations of top handle 60 are contemplated, including different shapes for alternate tool configurations (such as grippable handles for pliers or finger-insertable handles for scissors), and different material composition or coverings (such as rubber for grip enhancement).

Spring 100 is a standard flexible spring that has near the middle an interlocking pivotal point 110. Spring 100 has sufficient tension to maintain top handle 60 and bottom handle 70 in an open, neutral position until pressure is applied. Spring 100 is sufficiently elastic that minimal pressure is required to bring top handle 60 and bottom handle 70 together, and top handle 60 and bottom handle 90 will return to their open neutral position easily once pressure is removed.

Interlocking pivotal point 110 is a pivot point of spring 100 that allows spring 100 to flex and unflex without significantly moving from its neutral position.

Connectors 15, 25, 65, and 75 are threaded screw-type connectors that protrude from their respective bases as shown in FIG. 3. These connectors allow their connecting parts to be easily removed and interchanged for cleaning, sterilization, storage, or replacement. It should be understood that while threaded screw-type connectors are described and illustrated here, other connectors and connection receivers are contemplated and can be substituted, such as snap-in connectors.

Spring connector 90 and spring connector 100 are standard spring hold-down machine screws that allow their respective handles to be removed from spring 80 for cleaning, sterilization, storage, or replacement.

It should be understood that while a particular example embodiment is described here, many components can be substituted and varied without altering the character of this invention, and such substitutions and variations are contemplated and encouraged as an essential component of this invention. Such substitutions and variations include removal of the spring component for tools that do not require tension to hold the handles apart, alternate handles and handle configurations, alternate pivot means, and alternate jaw configurations such as surgical scissors or pliers, including such configurations where the alternate jaw 20 and the top handle 60 are rotatably connected about central pivot 50 in a similar manner to the first jaw (blade 10) and bottom handle 70.

FIGS. 5-8 illustrate some of the alternate component configurations. FIG. 5 depicts a jaw suitable for a set of pliers. FIG. 6 depicts a blade suitable for surgical scissors. FIG. 7 depicts a handle suitable for surgical scissors. FIG. 8 depicts a handle suitable for a set of pliers.

What is claimed is:

1. A hand tool, comprising:
    a base having a first face including a first threaded connection receiver and a second threaded connection receiver, and a second face including a third threaded connection receiver and a fourth threaded connection receiver;
    a jaw including an end having a threaded connector threadably engaging the first face of the base via the first threaded connection receiver;
    a blade including an end having a threaded connector threadably engaging the first face of the base via the second threaded connection receiver;
    a first curved handle including an end having a threaded connector threadably engaging the second face of the base via the third threaded connection receiver;
    a second curved handle including an end having a threaded connector threadably engaging the second face of the base via the fourth threaded connection receiver;
    a central pivot disposed through the base;
    a wire looped about the central pivot, the wire connecting the central pivot to the second threaded connection receiver and to the third threaded connection receiver; and
    a spring connecting the first curved handle to the second curved handle, the spring including a pivotal point where the spring pivots thereabout, wherein the spring maintains the first curved handle and the second curved handle in an open position.

2. The hand tool of claim 1, wherein the blade is a blade suitable for debulking fingernails or toenails.

3. The hand tool of claim 1, wherein the blade is a pliers jaw.

4. The hand tool of claim 1, wherein the jaw is a surgical scissors blade and the blade is a surgical scissors blade.

5. The hand tool of claim 1, wherein the blade is a surgical scissors blade.

6. The hand tool of claim 1, wherein the jaw is a pliers jaw.

7. The hand tool of claim 1, wherein the jaw includes a curved surface that faces the blade.

8. The hand tool of claim 7, wherein the curved surface of the jaw is rubber.

9. The hand tool of claim 7, wherein the jaw is rectangular-shaped and malleable.

10. The hand tool of claim 1, wherein the central pivot is disposed horizontally through a center of the base.

11. The hand tool of claim 1, wherein:
the first threaded connection receiver is disposed on a first end of the first face of the base and the second threaded connection receiver is disposed on a second end of the first face of the base, such that the first threaded connection receiver and the second threaded connection receiver are disposed on opposite sides of the first face of the base;
the third threaded connection receiver is disposed on a first end of the second face of the base and the fourth threaded connection receiver is disposed on a second end of the second face of the base, such that the third threaded connection receiver and the fourth threaded connection receiver are disposed on opposite sides of the second face of the base;
the first threaded connection receiver and the fourth threaded connection receiver are disposed diagonally relative to each other on the base; and
the second threaded connection receiver and the third threaded connection receiver are disposed diagonally relative to each other on the base.

12. The hand tool of claim 1, wherein the jaw tapers from the end having the threaded connector to a distal end.

13. The hand tool of claim 12, wherein the blade includes a surgical scissor blade having an arcuate end.

14. The hand tool of claim 13, wherein the first curved handle includes a finger hole.

15. The hand tool of claim 14, wherein the second curved handle includes a curved surface that faces the first curved handle.

16. The hand tool of claim 1, wherein the blade includes a length greater than a length of the jaw.

* * * * *